United States Patent [19]

Moser et al.

[11] Patent Number: 5,725,556
[45] Date of Patent: Mar. 10, 1998

[54] SUTURE LOCKING APPARATUS

[75] Inventors: Thomas V. Moser, Bedford; James P. Ryan, Amherst, both of N.H.

[73] Assignee: M & R Medical, Inc., Bedford, N.H.

[21] Appl. No.: 573,291

[22] Filed: Dec. 15, 1995

[51] Int. Cl.$^6$ .................................................. A61B 17/04
[52] U.S. Cl. ................................. 606/232; 128/898
[58] Field of Search ....................... 606/232, 73, 75, 606/148, 228; 623/13

[56] References Cited

U.S. PATENT DOCUMENTS

4,741,330  5/1988  Hayhurst ............................. 606/232
5,258,015  11/1993  Li et al. ............................... 606/232
5,370,661  12/1994  Branch ................................ 606/232

*Primary Examiner*—Glenn K. Dawson
*Attorney, Agent, or Firm*—William B. Ritchie

[57] ABSTRACT

A suture locking fastener for surgical procedures. The one piece plastic molded fastener features a plurality of triangular-shaped leaves that are attached to a base. At least one of the leaves is attached to the base using a flexible hinge section thus permitting that leaf to articulate with respect to the base. The leaves are positioned at a predetermined angle relative to the horizontal that is at least 30 degrees, and, preferably, 45 degrees which permits a suture, either a thread or a plastic filament, to be held securely without deforming or cutting into it.

18 Claims, 7 Drawing Sheets

SUTURE LOCKING APPARATUS

BACKGROUND OF THE INVENTION

1. Field of the Invention

The invention relates to surgical fasteners and method of using same.

2. Description of the Related Art

Advances in surgical techniques to repair orthopedic injuries have been exponential over the last decade. Arthroscopic surgery of knee injuries which used to cause the patient months of incapacitation and recuperation can now be accomplished with surgical procedures that are minimally invasive that result in a rapid recuperation. As a consequence, evaluation of all aspects of this type of surgery have been undertaken.

For example, it has recently been learned that menisci play an important role in having a fully functional knee joint, including tibiofemoral load transmission, shock absorption, lubrication, and passive stabilization of the knee joint. While it used to be commonplace to remove the menisci in a typical surgical procedure involving the knee when the menisci have been torn, surgeons today, recognizing the vital role of the menisci as an essential component of a normal knee, are aggressive in their attempts to conserve as much meniscal tissue as possible during any knee surgery. As a consequence, the efficient and rapid repair of meniscal tears is the uppermost goal of a surgeon performing such surgery.

The menisci are crescent shaped structures that are located medially and laterally in the knee joint, having bony attachments to the tibia at the anterior and posterior horns. Collagen fibers within the peripheral portion of the meniscus play a critical role in load transmission. The most peripheral portion of the meniscus is the meniscosynovial junction, which extends from the anterior to posterior horns. The orientation of the collagen fibers within the meniscus makes this structure particularly vulnerable to tearing when the knee joint is rotated and at the same time axially compressed, i.e., a "football" or "skiing" injury. Depending on the orientation of the patient's leg during the injury, the tear can damage either the transverse collagen fibers causing a longitudinal tear or the circumferential fibers causing a radial tear.

Surgical repair of the menisci is difficult due to several factors. The healing potential is dependent upon the vascular pathway that is present or that can be stimulated. Clearly, any surgical procedure that minimizes the involvement of tissues outside of the tear zone is likely to enjoy a better prognosis with respect to vascular supply than a procedure that is more invasive. Longitudinal tears in the vascular periphery of either meniscus have been found to heal and, thus, provide significant retention of the beneficial properties discussed above. However, repairs outside this region are inconclusive. While healing may occur, it is uncertain as to whether mechanical function can be restored as well.

The conditions necessary to heal a tear in a meniscal lesion are basically the same as with any repair of a musculoskeletal tissue. Thus, the surgeon will stabilize the torn area through suturing so that the tear does not increase and to successfully coapt the edges of the tear. Then, the injured limb is externally immobilized until the tear is healed.

To prevent neurovascular complications that can occur in such surgery, various surgical techniques have been explored. The "open" technique is suitable only for tears that are within 2 mm of the meniscosynovial junction. Most tears are repaired using arthroscopic techniques, categorized as either "outside-in", "inside-out" or "all inside". The "inside-out" technique was developed first. This procedure requires the surgeon to place spinal needles using arthroscopic visualization through both meniscal fragments and then out through the joint to exit percutaneously. The needles are used to introduce sutures that are used to stabilize the tear while it heals. While this procedure is usually quite successful, a small percentage of neurovascular complications was experienced as well as it requires a large incision.

The "outside-in" approach was developed to eliminate this problem. In this procedure, the surgeon utilizes spinal needles as in the "inside-out" technique. However, in this technique, safe passage of the needles is more easily controlled using knowledge of anatomical landmarks to avoid the peroneal nerve, for example. For a more detailed discussion of the meniscal anatomy and surgery, see, *Principles and Decision Making in Meniscal Surgery*, Alan P. Newman et al., *Arthroscopy: The Journal of Arthroscopic and Related Surgery* 9(1):33–51, incorporated herein by reference.

Common to these techniques is the placement of sutures that bring the two surfaces of the torn meniscus together so that healing may occur. As can be easily envisioned, tying knots in sutures while operating in extremely confined environment provided by the hollow needles requires incredible dexterity. Indeed, a substantial portion of the time required for the procedure is due to the time that it takes to place the sutures. Also, any method or apparatus that simplify and facilitates this procedure would significantly encourage more physicians to perform this type of surgery.

The typical "outside-in" procedure begins by directing a spinal needle from a percutaneous suturing "portal" that is "outside", and, then, directing the spinal needle through the capsule and both sides of the meniscus tear. The surgeon is able to view "inside" via an arthroscope inserted through a viewing "portal". Once the spinal needle spans the tear as seen through the arthroscope, an absorbable suture is delivered across the tear inside the knee through the needle. An "interference" knot is tied on the suture. An "interference" knot is several knots tied onto a knot such that the resulting knot is sufficiently large to prevent it from pulling from the opening in the tissue made by the needle. Next, the needle is removed with the suture left in place and the interference knot is pulled back into the knee through the suturing "portal" until the knot is positioned against the tear site. The process is then repeated several times until the tear is stabilized. The procedure is completed by tying all of the suture tails together through an incision under the skin outside of the knee joint. Tying the suture tails together, however, can place unwanted tension on the meniscus and could possibly cause further damage to the torn meniscus.

An alternative to the use of interference knots would be to retrieve the end of the suture in the joint by pulling the suture out through a second cannula and then tying the two ends.

Another alternative is the "all inside" technique involves either placing several interference knot or several T-FIX along the peripheral rim with two suture strands tied together using an arthroscopic knot passer. This is extremely technically demanding procedure. For a detailed discussion of these well known techniques, see *Arthroscopic "Outside-to-Inside" Meniscus Repair Technique*, Craig D. Morgan, *Techniques in Orthopaedics*, 8(2):99–104, incorporated herein by reference.

To increase the speed of this procedure as well as any surgical procedure where two or more tissue members must be fastened together, various surgical fasteners have been developed. To replace the "interference" knot, U.S. Pat. No. 4,669,473, issued to Richards et al. on Jun. 2, 1987, discloses a T-bar fastener that is attached to a suture. The T-bar fastener is designed to anchor into bone using a special tool.

U.S. Pat. No. 5,258,015, issued to Li et al., discloses another surgical device that is intended to be used for such procedures. The device is designed to be used with a smooth surface plastic fastener such as taught in U.S. Pat. No. 4,669,473. The device features at least one, but preferably two locking flaps, with each locking flap having a series of engaging teeth at its locking end. The device is mounted upon the smooth surfaced plastic fastener with the fastener tensioned against the device. A special tool depresses the locking flaps inwardly thus causing the teeth to engage the plastic fastener and deforming it. Foot members on the bottom of the device keep the device from rotating once in position. This device is not suitable for use with suture threads. Moreover, since the plastic fastener must be less dense than the locking flaps in order for the device to hold, the strength of either the plastic fastener or the locking flaps must be compromised.

U.S. Pat. No. 5,372,146, issued to Branch, discloses another variation of a tissue fastening apparatus. In this device, a plurality of spherical protrusions are spaced along a smooth filament. A head member has a flange that deforms to permit the device to move in one direction only. As found with the Li apparatus, the use of a plastic fastener is essential. As sutures must be extremely small in cross-sectional diameter, any small variation or imperfection in the construction of the plastic fastener will result in a weak spot that easily breaks. Tests of all such plastic fastener members have found them to be unreliable and, therefore, not suitable for use in surgery since a broken "suture" can mean the difference between a successful operation and one that has to be redone.

Still another variation is the slotted suture anchor disclosed in U.S. Pat. No. 5,269,809, issued to Hayhurst et al. on Dec. 14, 1993. This disclosure is a variation of the T-fastener discussed above. This device features a hollow cylindrical sleeve with a slot extending about half the length of the sleeve. The slot serves to hold a suture thread or a plastic fastener and provide a T-shaped structure that anchors the suture in the tissue. The suture is fed into the sleeve and exits the slot. The thread is prevented from exiting by the use of one or more interference knots. Similarly, the plastic filament or braided multi-filament is held within the sleeve via a locking washer that is molded into the plastic fastener.

There is not found in the prior art a suture locking apparatus that can be used with a standard suture and that meets the critical size, strength, and ease of use requirements that must be met with arthroscopic surgery, particularly surgery of the knee calling for meniscus repair.

SUMMARY OF THE INVENTION

It is an aspect of the invention to provide a suture locking apparatus that eliminates the need for tying knots during surgery, particularly arthroscopic surgery.

It is another aspect of the invention to provide a suture locking apparatus that grips the suture as a result of the structure of the apparatus.

It is still another aspect of the invention to provide a suture locking apparatus that will easily pass a series of knots on a suture or a series of "beads" or other protrusions on a suture in one direction but will not pass the knots or "beads" in reverse direction.

Another aspect of the invention is to provide a suture locking apparatus that can be used with a suture having pretied knots that will secure two or more tissue members together.

It is another aspect of the invention to provide a suture locking apparatus that can be used with mono-filament or multi-filament or silk sutures, either fitted with knots or a plastic protrusions, which will serve to lock the filament to the suture locking apparatus thus holding two or more tissue members together.

It is still another aspect of the invention to provide a suture locking apparatus that has at least one rigid articulating leaf such that when the suture or filament is tensioned against the leaf, the leaf collapses toward the center of the suture locking apparatus thus providing a greater gripping force of the suture or filament.

It is still another aspect of the invention to provide a suture locking apparatus with a plurality of leaves at a substantial positive angle measured from the horizontal base of the apparatus when the leaves is locked holding a suture or a filament.

Another aspect of the invention is to provide a suture locking apparatus that has four leaves.

Another aspect of the invention is to provide a tool holder for the suture locking apparatus tool such that the tool holder can easily maneuver the suture locking apparatus into position.

Another aspect of the invention is to provide a suture locking apparatus that joins the leaves to the apparatus via a flexible hinging section.

Another aspect of the invention is to provide a suture locking apparatus where each leaf has a structure where the leaf engages the suture or filament that increases the "grabbing" ability of the leaf to hold the suture or filament.

It is an aspect of the invention to provide a suture locking apparatus that features a cone-shaped structure on the under side surface of the apparatus which serves to lead the suture or filament into the opening of the apparatus.

Finally, it is an aspect of the invention to provide a method of suturing that is suitable for use where standard sutures are preferred but are difficult to use due to the limited space available for the tying of knots.

The invention is a suture locking apparatus that replaces the need to tie knots during surgery, particularly arthroscopic surgery. A series of knots are pre-tied on a standard suture thread during manufacture. The knots spaced at approximately 1 to 1.5 mm apart. The suture can be mono-filament, multi-filament, or silk. "Beads" or other protrusions can be used in the place of knots and the use of the term "knot(s)" is meant to include such structures. The "beads" or other protrusions can be either molded as an integral part of a "plastic" suture or added to an existing suture by techniques known in the art. The positioning of the knot section, the length of the knot section, and even the number of knot sections and spacing on a suture will be determined in accordance with the type of surgical procedure that is to be preformed. Also, the distal end can be fitted with a T-FIX or other anchoring device well known in the art, if desired. The suture locking apparatus has a base, defining a horizontal plane. The cross-sectional shape of the base is not critical and the base itself can be round, octagonal, hexagonal etc., as long as it provides an annulus in which one or more rigid leaves may be fastened thereto. The rigid leaves are preferably attached to the base via a flexible hinging section to permit flexing. Each leaf is preferably triangular shaped defining a funnel shaped suture lead-in cone at the bottom surface of the leaves. At the apex of the triangle, the leaves define an area that is designed to hold a suture having a series of knots that is fed therethrough. Alternatively, a suture having a series of protrusions such as "beads", either molded in or attached thereto can also be used. The funnel-shaped cone makes it easy to spread the leaves to feed the knotted suture through the apparatus. Preferably, the apex may be fitted with a slight radius, corresponding to the diameter of the suture such that leaves when fitted together will hold the knotted suture securely without deforming or cutting into the suture so as to cause it break prematurely. Each leaf is mounted on the base at a substantial positive angle measured from the horizontal plane by the bottom surface of the base. The angle ranges from 10 degrees to 50 degrees but is preferably about 30 degrees, although an approximately 45 degrees is expected to provide the maximum holding strength. The 30 degree angle is preferable because it reduces the overall height of apparatus. Use of an alternative embodiment which reduces the overall height of the apparatus may result in the use of the 45 degree angle as preferable for that variation. An optional plurality of spikes on the bottom surface of the base may be used to prevent the apparatus from rotating once it is positioned.

In use, the knotted suture will easily pass through the apparatus in one direction but will be locked when the apparatus is tensioned because the leaves collapse in tension against the tissue via the knotted suture. In use, the knotted suture is placed in the tissue members that are to be fastened together with the distal end attached thereto. The proximal end of the suture is then fed through the suture locking apparatus which is held in the suture locking apparatus tool which is used to place the suture locking apparatus against the surface of the proximal tissue that is to be fastened. The surgeon then tensions the suture to the desired amount, and, then, uses the tool to slide the suture locking apparatus down the suture until it is positioned against the tissue with a knot locking the apparatus on the suture. Then, the tool is removed, and the suture is trimmed to a desired length.

The use of invention makes any meniscal repair easier for the above-described arthroscopic meniscal repair, that is, "outside" etc. with advantage minimizes incision size and eliminates knots. During the procedure to repair the meniscal tear, the surgeon passes a suture through the margins of the tear that are to be fastened together. The suture has a series of spaced apart interference knots. The suture locking fastener will have at least one rigid articulated leaf set at a predetermined angle relative to the suture locking fastener. The suture locking fastener is aligned to one of the tissue members such that said suture locking fastener is centered over a point defined by said suture exiting that tissue member and such that said suture can pass through said suture locking fastener when said suture locking fastener contacts that tissue member. The surgeon then tensions the suture within the tissue members. Next, the surgeon slides the suture locking fastener over the suture. As each knot encounters the suture locking fastener, the knot causes the articulated leaf of the fastener to articulate. Finally, the fastener is locked onto the suture via one of the knots such that said suture locking fastener contacts one of the tissue members and such that one knot of said suture thread firmly engages the leaf of said suture locking fastener whereby the tissue members are stably fastened together. The suture locking apparatus is also useful for any surgical technique in soft tissue, ligament, tendon or bone repair.

DETAILED DESCRIPTION OF THE INVENTION

Figure 1:
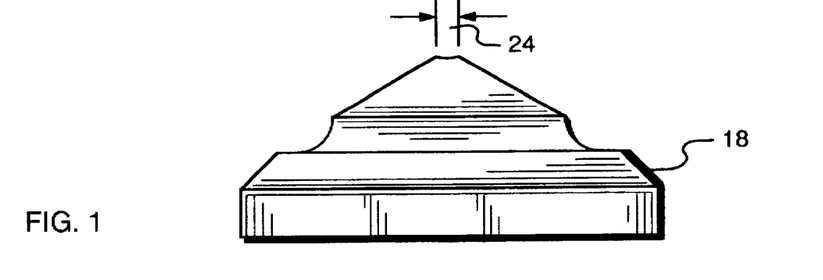
FIG. 1 is a side view of the preferred embodiment of the suture locking apparatus.
Figure 2:
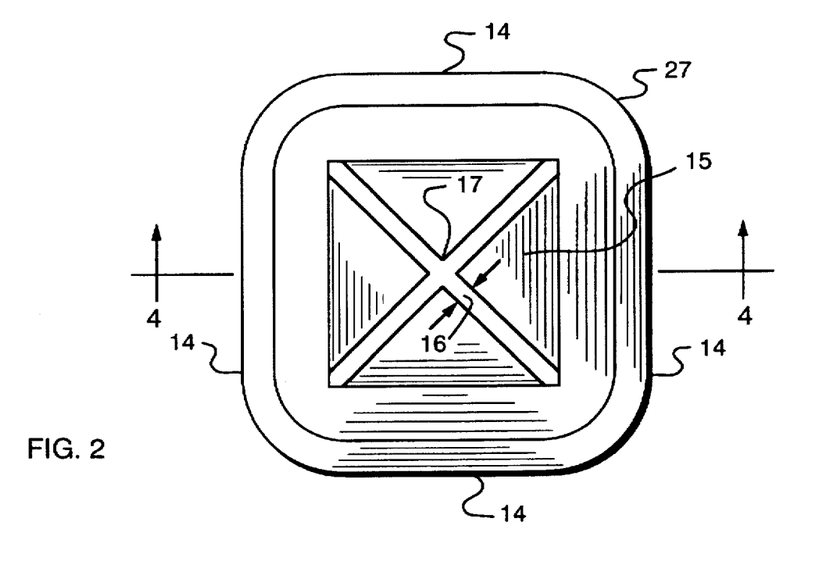
FIG. 2 is a top view of the suture locking apparatus.
Figure 3:
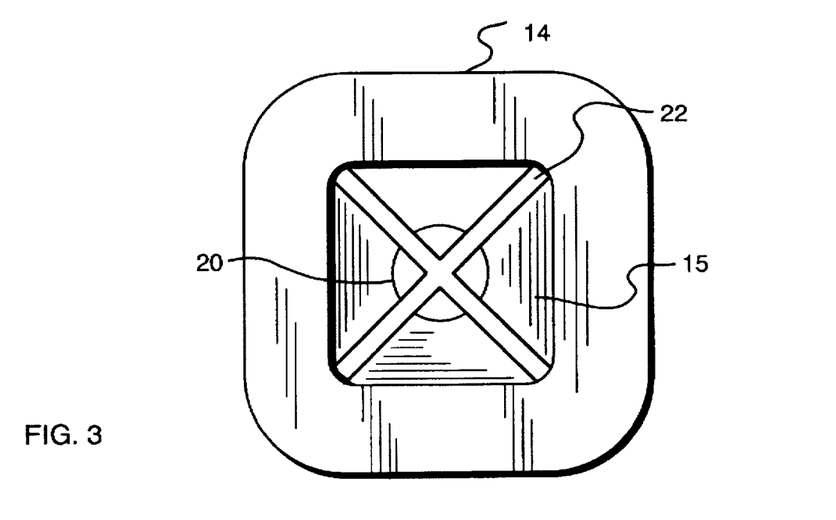
FIG. 3 is bottom view of the suture locking apparatus.
Figure 4:
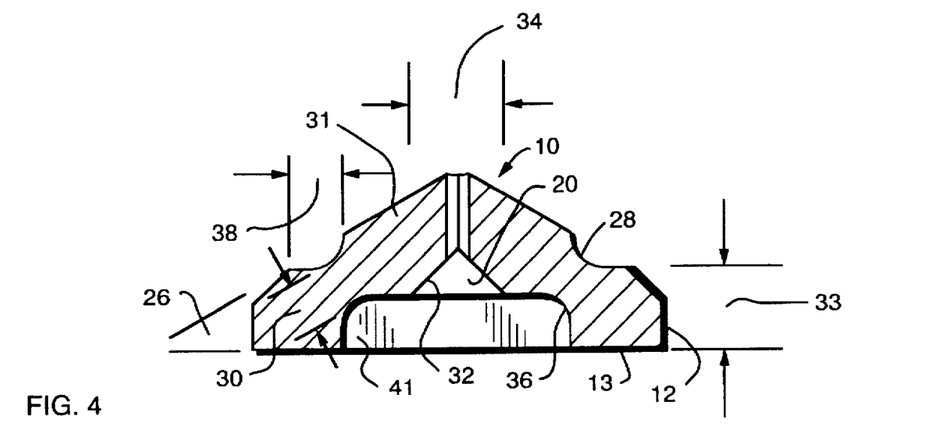
FIG. 4 is a cross-sectional view of the preferred embodiment across section lines 4—4 in FIG. 2.
Figure 5:
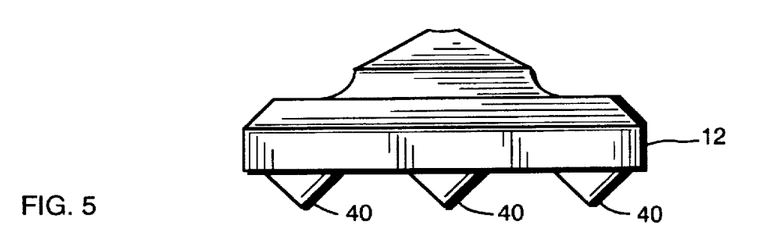
FIG. 5 is a side view of an alternative embodiment of the suture locking apparatus.
Figure 6:
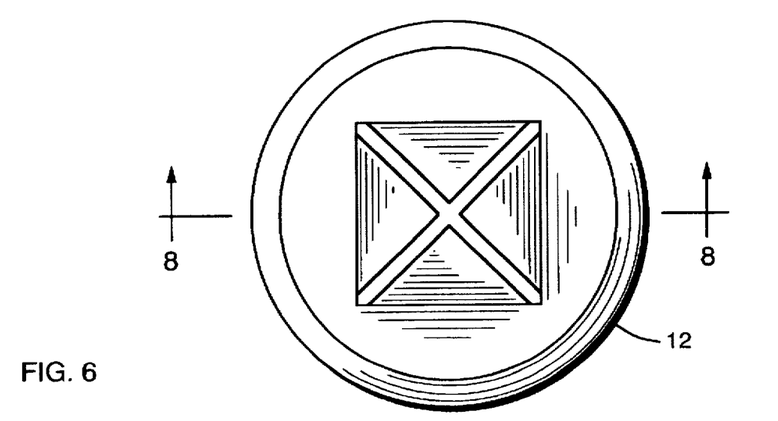
FIG. 6 is a top view of the alternative embodiment.
Figure 7:
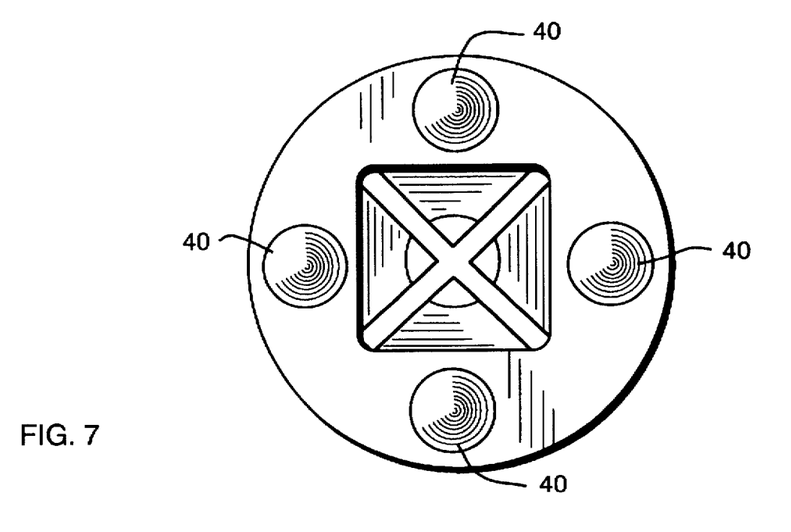
FIG. 7 is bottom view of the alternative embodiment.
Figure 8:
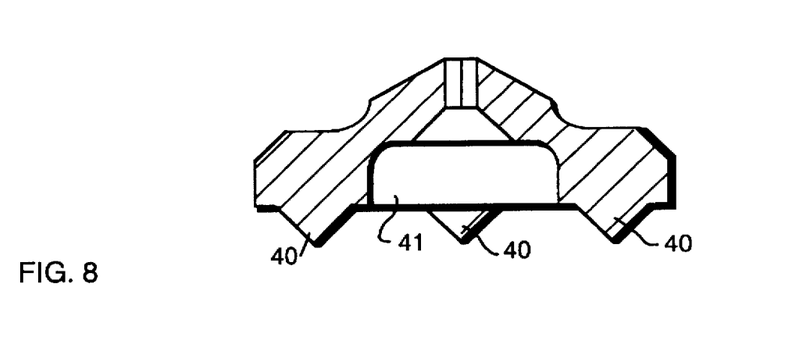
FIG. 8 is a cross-sectional view of the alternative embodiment across section lines 8—8 in FIG. 6.

Referring now to FIGS. 1–4, the preferred embodiment of the invention is described. The following dimensions represent the preferred value for the invention when sized to meet the requirements of arthroscopic meniscal repair. However, a different surgical procedure for this type of injury or a surgical procedure involving different tissue members may require changing these dimensions accordingly. Invention 10 is preferable square-shaped where side 14 is about 120 thousands of an inch as shown in FIGS. 2 and 3. Sides 14 meet in radius 27 which is preferably about 30 thousandths of an inch. However, other shapes are also acceptable such as round, octagonal, hexagonal, etc. Invention 10 is preferably injection molded using an absorbable plastic such as polylactide copolymer or a glycide copolymer that are well known in the art. If a non-absorbable plastic is preferred, then invention 10 may be fabricated from any suitable medical grade plastic.

Base 12 defines a horizontal plane along bottom 13. Base 12 preferably has a thickness 33 that is 25 thousandths of an inch. In the preferred embodiment, four substantially identical leaves 15 are attached to base 12 via flexible hinging section 31. While the number of leaves is preferably four, as noted below one leaf (shown in FIG. 16), two leaves (not shown), or three leaves (shown in FIG. 17) could also be utilized. One or more of the leaves can be non-articulating as discussed below (FIG. 16) or free to articulate as in the preferred embodiment. Leaves 15 are attached at angle 26 to form a pyramidal structure. Regardless of the number of leaves 15, and irrespective as to whether or not one or more is articulating, leaves 15 will always form a polyhedron shape. While the exact number of degrees of angle 26 is not critical, it should be greater than 10 degrees but less than 50, with 45 degrees being expected to provide the greatest holding power, yet 30 degrees being preferable for this embodiment due to the lower profile provided. Spacing 16 between the respective leaves 15 is preferably about 7 thousandths of an inch. Chamfer 18 is preferably about 0.01×45 degrees. As shown in FIG. 2, the apex 17 of leaves 15 are pointed and leave a space 24 that is approximately 10 thousandths of an inch which is preferable for small diameter suture threads. However, if larger diameter sutures are used, apex 17 could also be radiused to match the diameter of the suture such as radius 94 as shown in FIG. 17. Space 24 would, therefore, be adjusted accordingly.

Cone 20 is provided by the bottom surfaces 32 of leaves 15. Cone 20 serves to help lead the knotted suture threads through invention 10. Once a knot in the suture contacts cone 20, leaves 15 are spread apart and the knotted suture thread passes easily therethrough. Base 34 of cone 20 is preferably about 30 thousandths of an inch in diameter.

The principle difficulty with many prior art devices that have been tried for such purposes is that the devices have failed to hold the suture. As noted above, the angle 26 must be greater than 10. Another critical aspect of invention 10 is the use of section 31 to connect the leaves 15 to base 12. The flexing of hinge 31 occurs at approximately 16 thousandths of an inch from the bottom 13 with leaves 15 being rigid. Radius 28 is preferably about 20 thousandths of an inch, while radius 36 is preferably 10 thousandths of an inch. Hinge 31 is consequently about 15 thousandths of an inch thick in region 30. The width 38 of top recess is preferably about 20 thousandths of an inch. Constructed in this manner, hinge 31 can be flexed easily.

Referring now to FIGS. 5–8, an alternative embodiment of invention 10 is shown. In this embodiment, base 12 is now shown as circular having a preferable radius of about 60 thousandths of an inch. The other dimensions concerning the leaves, base thickness, flexible hinge section, etc. remain as above. This embodiment also shows the addition of a plurality of cone-shaped teeth 40. Each tooth 40 has a preferable diameter of about 30 thousandths of an inch. While teeth 40 are shown in this embodiment, teeth 40 could also be used with the preferred embodiment as depicted in FIGS. 1–4. Also, the shape of teeth 40 could be changed as long as teeth 40 prevent invention 10 from rotating while invention 10 is locked in position holding a knotted suture thread.

Figure 9:
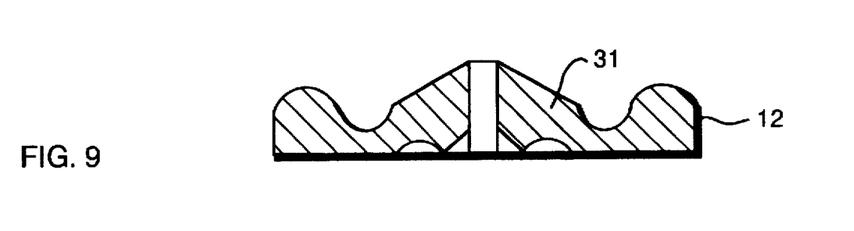
FIG. 9 is a cross-sectional view of another alternative embodiment.

FIG. 9 is a cross-sectional view of another alternative embodiment. In this embodiment, base 12 has been configured to eliminate much of recess 41 (shown in FIGS. 4 and 8), thus reducing the overall height of invention 10 to approximately 36 thousandths of an inch. Sufficient room must still be provided to allow for clearance so that the leaves 15 can flex. If recess 41 is eliminated, then, the overall outside dimension of invention 10 must be correspondingly increased. The expected remaining dimensions of the remaining components would remain as substantially as specified for the preferred embodiment. Angle 26 for this embodiment could extended beyond 30 degrees to increase the holding power but not exceeding 45 degrees.

Figure 10:
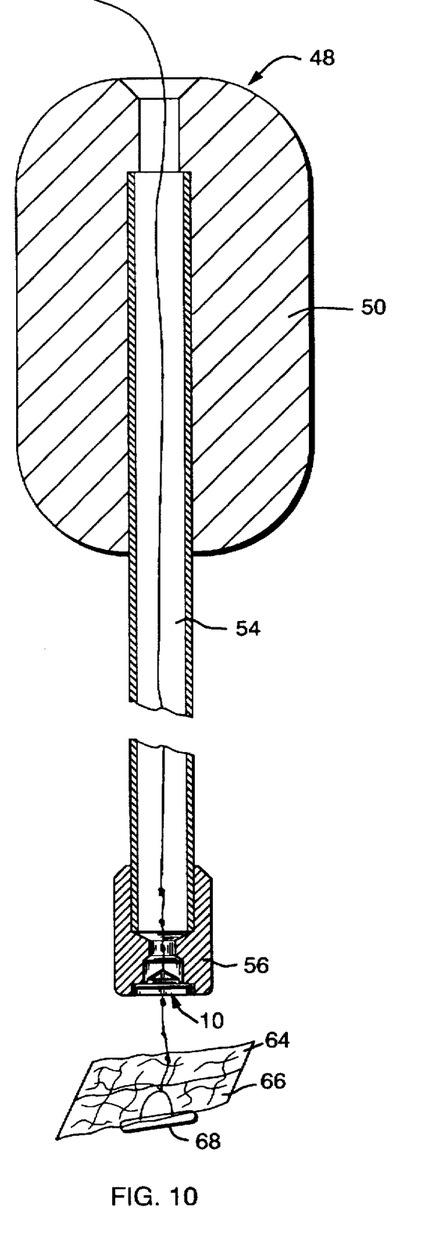
FIG. 10 is a cross-sectional view of the suture locking apparatus being placed in position via the corresponding suture locking apparatus placement tool.
Figure 11:
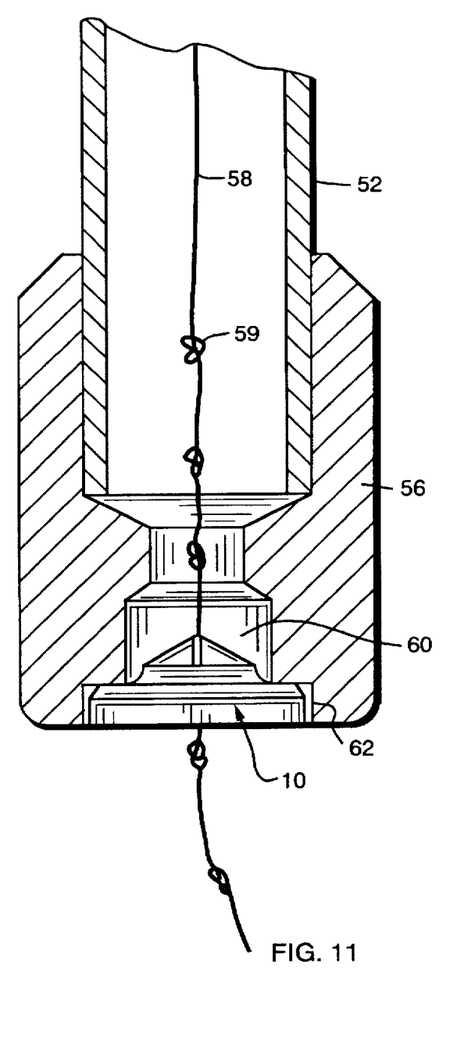
FIG. 11 is a detailed cross-sectional view of the placement tool.

Referring now to FIGS. 10 and 11, a cross-sectional view of tool 48 is provided. The purpose of tool 48 is to hold invention 10 so that the surgeon can accurately position invention 10 against tissue member 64 that is being sutured to tissue member 66. As shown, suture thread 58 is provided with a series of spaced knots 59. One of knots 59 will serve to lock invention 10 firmly to suture 58 thus keeping tissues 64 and 66 in close proximity to one another so that healing may occur. In this example, the distal end of suture 58 is held by use of T-FIX 68. Handle 50 features recess 54 which permits suture 58 to be threaded through. Handle 50 is sized to be comfortable to hold. Since tool 48 is to be used in a surgical environment, all materials used must be capable of being cleaned and sterilized. Inserted into recess 54 is extension tube 52. The length of tube 52 must be long enough to keep the suture relatively straight as it passses through the suture locking apparatus. Fitted on the end of extension tube 52 is the suture locking apparatus holder 56. Holder 56 has a centered recess 62 which is dimensioned to correspond to base 12 of invention 10. An easily releasable fit between invention 10 and recess 62 is required so that invention 10 will stay within tool 48 until it is placed in position but can be easily released once suture 58 has been tensioned against T-FIX 68. Recess 60 is immediately adjacent to recess 62 and is dimensioned to provide sufficient room to allow for the leaf structure to flex as the suture knot 59 is pulled through invention 10.

Figure 12:
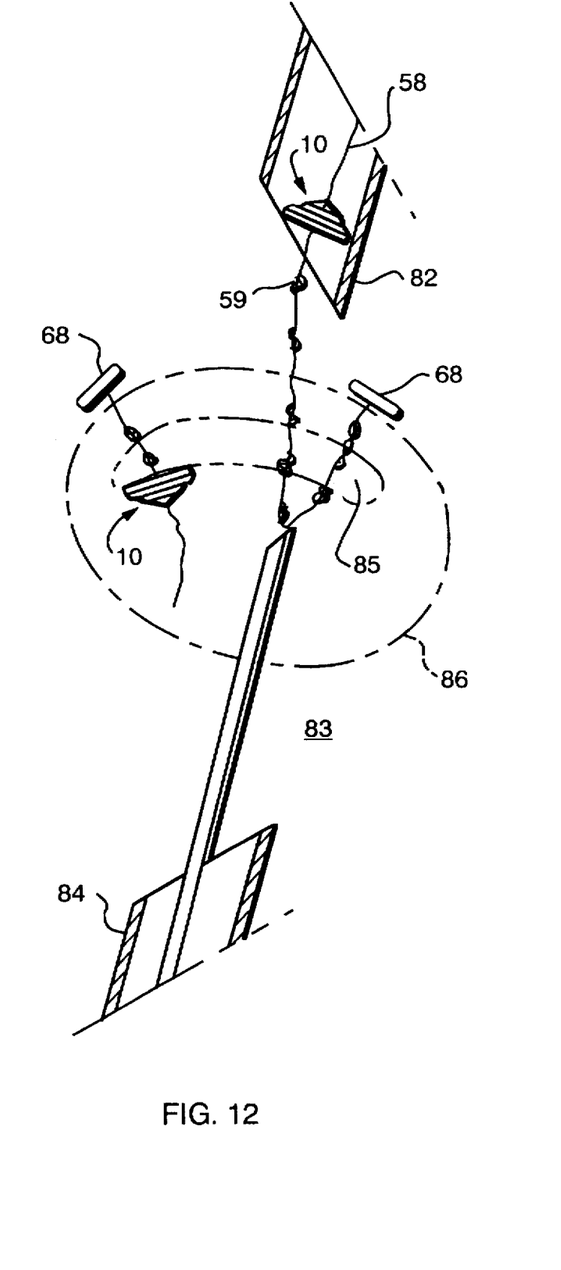
FIG. 12 is an illustration of the suture locking apparatus being used to suture a typical meniscal repair.
Figure 13:
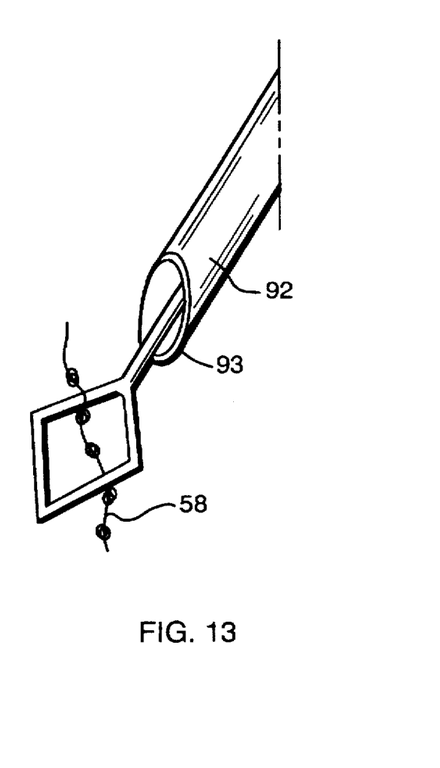
FIG. 13 is an isometric view of a modified suture grabber for use with the suture locking apparatus.

FIG. 12 is cross-sectional illustration of the suture locking apparatus being used to suture a typical meniscal repair. As noted above, the preferable method for repairing a meniscal tear is the "outside-to-inside" technique. The use of invention 10 eliminates the need for the surgeon to tie any knots. Cannula 82 is inserted into the knee 83. Cannula 84 is then inserted into approximate center of the meniscal tear 85, just outside of the meniscus 86. Through the cannula 82, suture 58, which is fitted with a series of knots 59 as described above with T-FIX 68 attached at the distal end, is inserted through the tear 85. Through the cannula 84, a suture grabber 92 (shown in FIG. 13) is inserted and the free end of the suture thread 58 is picked up and brought within close proximity to the cannula 82. Since suture grabber 92 must be able to penetrate the tissue of meniscus, suture grabber 92 must be provided with sharpened point 93 at the end. Then, the proximal end of the suture 58 is inserted through the suture locking apparatus 10 out the handle 50 of the placement tool 48 (shown in FIG. 10). Then, the surgeon can fasten the suture locking apparatus 10 as described above. Note that suture locking apparatus 10 can be fastened on the opposite side of the tear as T-FIX 68, shown on the left, or on the same side of the tear as T-FIX 68 as shown on the right.

Figure 14:
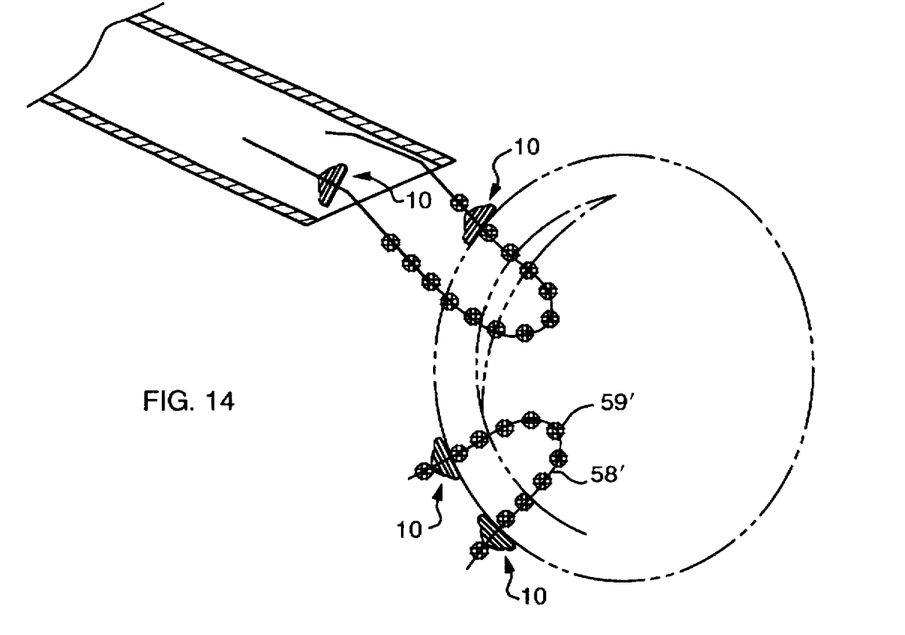
FIG. 14 is a cross-sectional illustration of surgical repair of a meniscus with one suture in place and the second suture about to be positioned.
Figure 15:
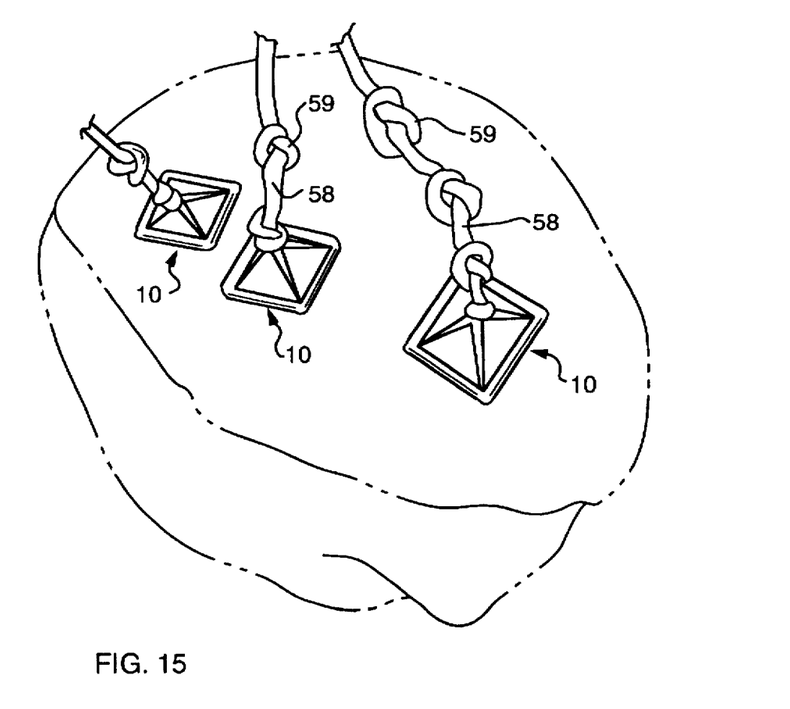
FIG. 15 is an illustration of the three suture locking apparatus in a locked position before the knotted suture thread has been trimmed.

FIG. 14 is cross-sectional view with one suture in place and a second one about to be fastened. In this situation, both sutures have been fastened using a suture locking apparatus 10 on each end, i.e., the T-FIX 68 has been eliminated. Instead of suture thread, plastic filament 58' with protrusions 59' are used or beads are molded onto an existing suture, either a monofilament or a multi-filament. In FIG. 15, an illustration of the three suture locking apparatus 10 is shown in position along a meniscus tear prior to trimming sutures 58.

Figure 16:
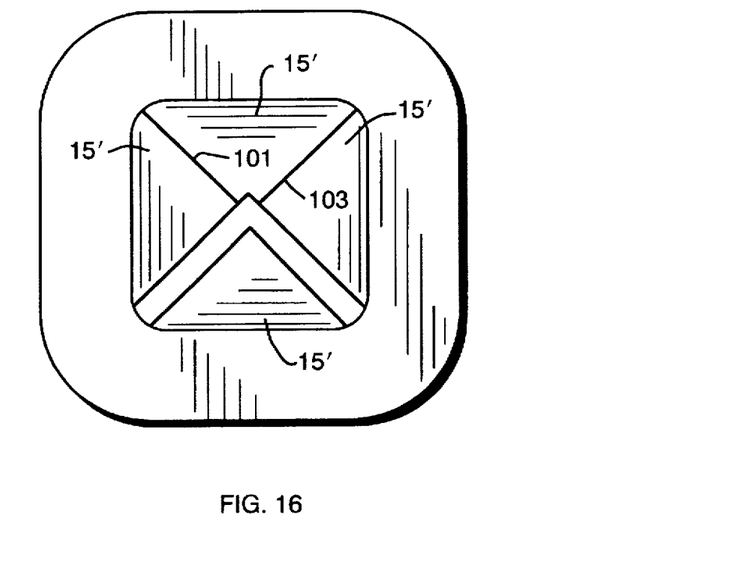
FIG. 16 is a top view of single leaf alternative embodiment of the suture locking apparatus.
Figure 17:
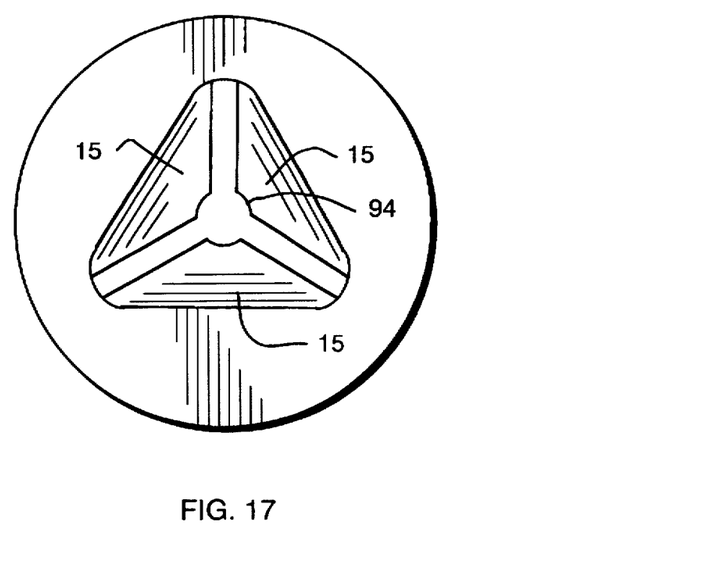
FIG. 17 is a top view of triple leaf embodiment for use with a plastic filament fastener.

FIG. 16 is a top view of a single leaf embodiment of invention 10. In this embodiment, the leaf 15 is the only leaf that is permitted to articulate via a flexible hinge section. Leaves 15' are attached to another along joints 101 and 103 and therefore held in place. As with the other embodiment, dimensions are adjusted to meet the expected size of suture thread that is to be used. FIG. 17 is a top view of a three leafed suture locking apparatus with the apex of the leaves radiused to accommodate a larger sized suture thread. Either one, two, or three leaves could be articulating, that is, attached to base 12 using a flexible hinge section. While it is expected that the device will most commonly be used with knotted suture thread, it is not so limited as shown in FIG. 14.

If a filament is developed that eliminates the breaking problems discussed above, then such a filament could be used with the invention, providing the dimensions of the leaves, space between the leaves at the apex, geometry of the leaf apex were adjusted using the principles described herein to enable the invention to hold such a filament.

While there have been described what are at present considered to be the preferred embodiments of this invention, it will be obvious to those skilled in the art that various changes and modifications may be made therein without departing from the invention and it is, therefore, aimed to cover all such changes and modifications as fall within the true spirit and scope of the invention.

What is claimed is:

1. A suture locking apparatus for use with a suture having a diameter and a plurality of spaced apart protrusions, said suture locking apparatus comprising:
   a base member having a horizontal plane and an aperture therethrough, said aperture having an attachment surface;
   a plurality of substantially rigid, triangular-shaped leaves, each of said leaves having a top and bottom surface, each of said triangular-shaped leaves having a base and an apex, and each of said leaves further having an attachment region, adjacent to said base; wherein, each of said leaves is attached to said base member at the attachment surface of said base member via said attachment region, such that said leaves form a polyhedron with the apex of each leaf immediately adjacent to the apex of the other, thus, said leaves providing a suture opening; and wherein at least one of said leaves articulates with said base, and with each leaf in an unstressed state having an angle defined by a plane coincident with the top surface of that leaf and said horizontal plane of said base, wherein the angle of each leaf is substantially equal to the angle of the other leaves and the angle of each leaf ranges from at least ten degrees but less than fifty degrees.

2. The suture locking apparatus of claim 1 wherein said leaves articulate with said base member via a flexible hinge section.

3. The suture locking apparatus of claim 1 wherein the angle is thirty degrees.

4. The suture locking apparatus of claim 1 wherein said apparatus is a single piece of molded plastic.

5. The suture locking apparatus of claim 1 wherein the number of leaves is at least four.

6. The suture locking apparatus of claim 1 wherein the number of leaves is three.

7. The suture locking apparatus of claim 1 wherein each bottom surface of each leaf defines a conical-shaped recess having an apex with the apex of said conical-shaped recess being substantial coincident with said suture opening.

8. The suture locking apparatus of claim 1 wherein said suture opening is dimensioned in accordance with the diameter of said suture.

9. The suture locking apparatus of claim 1 wherein the suture is a flexible member that can be knotted, and, wherein, the plurality of spaced apart protrusions are knots tied onto the member, said suture locking apparatus having said suture opening dimensioned to lock said apparatus to the suture via one of the knots.

10. The suture locking apparatus of claim 1 wherein the suture is a plastic filament, and, wherein, the plurality of spaced apart protrusions are regions of enlargement integral with the filament, said suture locking apparatus having said suture opening dimensioned to lock said apparatus to the filament via one of the regions of enlargement.

11. The suture locking apparatus of claim 1 wherein the suture is a flexible member that can be knotted, and wherein the plurality of spaced apart protrusions are substantially spherical structures that are attached to the flexible member, said suture locking apparatus having said suture opening dimensioned to lock said apparatus to the flexible member via one of the spherical structures.

12. A positioning tool for a suture locking apparatus as claimed in claim 1, said positioning tool comprising:
   a handle having a top end and a bottom end, also having an axial length with an opening therethrough,
   an extension tube having a suture end and a handle end, also having an axial length with an opening therethrough, wherein said opening of said handle and the opening of said extension tube communicates with one another, the handle end of said extension tube being attached to the bottom end of said handle;
   an apparatus holder having a top end and a bottom end, the top end being attached to the suture end of said extension tube, said holder having a suture locking apparatus recess adjacent to the bottom end, and also having an opening extending from the bottom end to the top end and in communication with the opening of said extension tube, said holder also having a first recess that corresponds to the geometry of the base member of said suture locking apparatus and a second recess that corresponds to the polyhedron formed by said leaves, wherein the first recess is dimensioned to releasably hold said suture locking apparatus such that said suture locking apparatus will be held while said suture locking apparatus is being positioned but will be easily released once said suture locking apparatus has been positioned, and wherein the second recess is dimensioned to be sufficiently larger than the polyhedron formed by said leaves such that said leaves are free to articulate with said base member of said suture locking apparatus when a suture is passed through the bottom of said holder through the suture opening of said suture locking apparatus, through said extension tube and handle, and exits the top end of said handle.

13. A method of fastening at least two tissue members during a surgical procedure comprising the steps of:
   providing a suture locking fastener with at least one rigid articulated leaf set at a predetermined angle relative to a base of said suture locking fastener when said leaf is in an unstressed state; tying a series of spaced apart interference knots along a length of the suture;
   passing said suture through the tissue members;
   aligning said suture locking fastener to one of the tissue members such that said suture locking fastener is centered over a point defined by said suture exiting that tissue member and such that said can pass through said suture locking fastener when said suture locking fastener contacts that tissue member;

tensioning said suture within the tissue members;

sliding said suture locking fastener over said suture wherein each knot encountered by said suture locking fastener causes said articulated leaf to articulate;

locking said suture locking fastener onto said suture via one of the knots such that said suture locking fastener contacts one of the tissue members and such that one knot of said suture thread firmly engages the leaf of said suture locking fastener whereby the tissue members are stably fastened together.

14. The method of claim 13 wherein the tissue members are menisci and the surgical procedure is arthroscopic surgery.

15. The method of claim 13 wherein the arthroscopic surgery utilizes an "outside-inside" technique.

16. The method of claim 13 further comprising the steps of repeating the aligning, tensioning, sliding and locking steps with a second suture locking fastener on the same suture.

17. The method of claim 16 wherein said second suture locking fastener contacts a different tissue member than the tissue member contacted by said first suture locking fastener.

18. The method of claim 16 wherein said second suture locking fastener contacts the same tissue member as said first suture locking fastener.

* * * * *